United States Patent [19]

Bianco

[11] 4,226,238
[45] Oct. 7, 1980

[54] DISPOSABLE DIAPER

[75] Inventor: Carlo Bianco, Pescara, Italy

[73] Assignee: Fameccanica S.p.A., Italy

[21] Appl. No.: 957,063

[22] Filed: Nov. 3, 1978

[30] Foreign Application Priority Data

Jun. 5, 1978 [IT] Italy ............................ 24191 A/78

[51] Int. Cl.³ .......................................... A61F 13/16
[52] U.S. Cl. .................................................. 128/287
[58] Field of Search .............. 128/284, 286, 287, 288, 128/290 R, 290 H

[56] References Cited

U.S. PATENT DOCUMENTS

| | | | |
|---|---|---|---|
| 2,905,581 | 9/1959 | Maxey | 128/288 |
| 3,527,221 | 9/1970 | Croon et al. | 128/287 |
| 3,639,917 | 2/1972 | Althouse | 128/284 |
| 3,828,784 | 8/1974 | Zoephel | 128/287 |
| 4,050,462 | 9/1977 | Woon et al. | 128/287 |
| 4,069,822 | 1/1978 | Buell | 128/287 |
| 4,119,450 | 10/1978 | Bianco | 128/287 |

FOREIGN PATENT DOCUMENTS 2215178 8/1974 France ............................ 128/287
1164469 9/1969 United Kingdom ............ 128/287

*Primary Examiner*—C. Fred Rosenbaum
*Attorney, Agent, or Firm*—McGlew and Tuttle

[57] ABSTRACT

A diaper comprises an outer sheet of waterproof plastic material having a deformed recess area between the sides and ends thereof which forms a pad receiving cavity which is bordered by marginal areas on each side and end. The cavity is about an inch deep and includes a bottom which is advantageously provided with corrugations or pleats which facilitate its expansion or distortion during wearing. An absorbent pad is disposed in the cavity, and a moisture holding strip of plastic material overlies at least a part of the marginal area on each side of the cavity and at least a portion of each side of the pad. The strip is welded to the marginal areas, and as a feature of the construction the plastic is stretched relative to the outer sheet and held in a stretched condition during welding so as to impart some resilient characteristics to the area which is adapted to be engaged around the legs of the wearer. Because the strip overlies the cavity, it aids in securing the pad in position and it insures that any liquid such as urine which may collect in the pad will not run out of the cavity.

16 Claims, 4 Drawing Figures

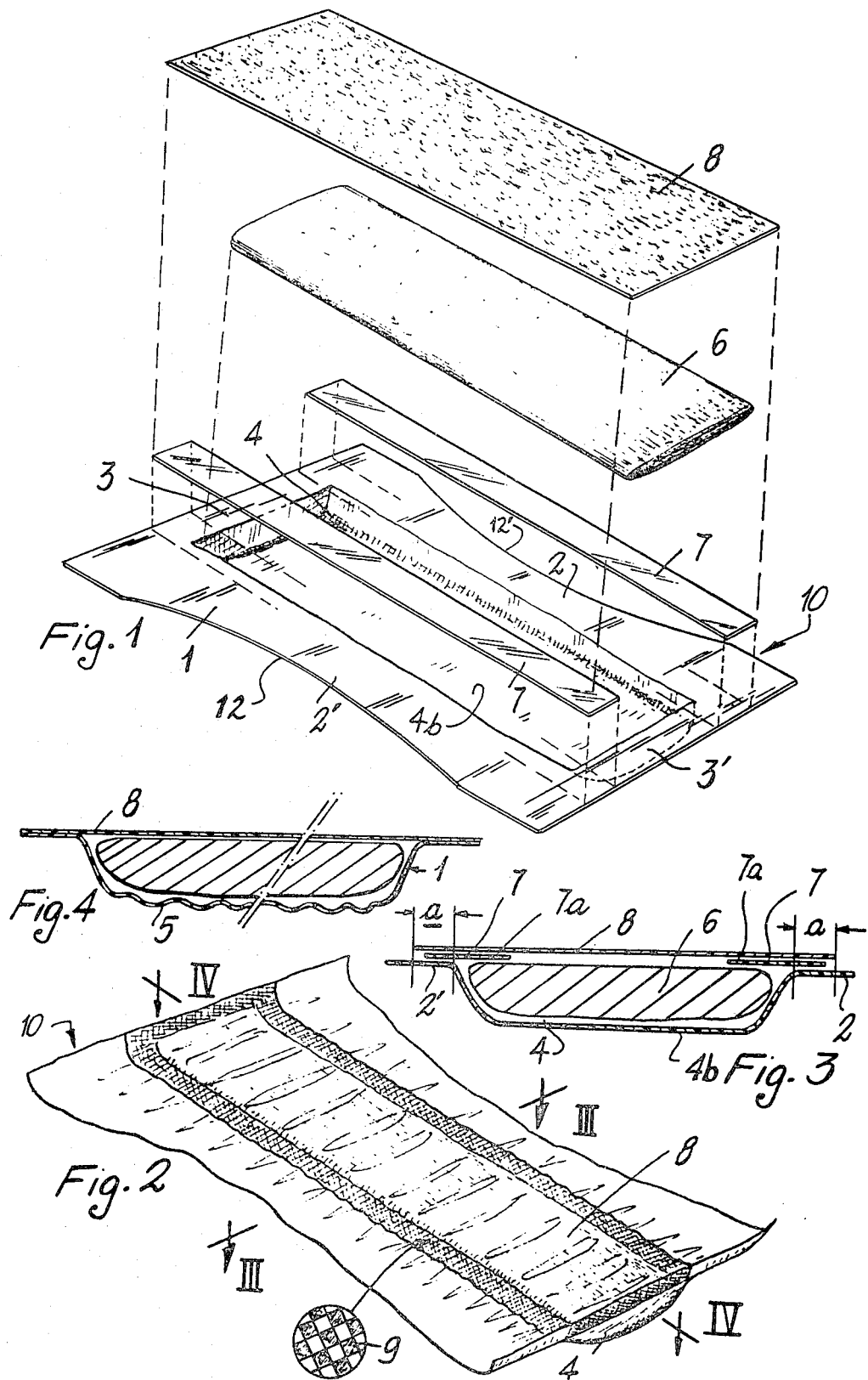

DISPOSABLE DIAPER

BACKGROUND OF THE INVENTION

1. Field of the Invention

This invention relates in general to the construction of diapers, and in particular to a new and useful diaper made of a plastic material and having a moisture cavity formed intermediate the sides and ends of an outer plastic sheet which has a pad therein and includes a moisture holding strip which extends along the marginal areas and is welded to and has a free portion overlying the pad to retain any moisture which may collect in the cavity.

2. Description of the Prior Art

A diaper similar to the present invention is shown and described in an Italian Patent Application No. 21990A-75 filed on Apr. 4, 1975 by the same Applicant in Italy. This diaper comprises an outer shield of waterproof material with an inner layer of absorbent material and finally a further inner water-permeable layer substantially coextensive with the outer web and sealed onto the outer web to thus confine the absorbent material in a complete manner between the outer web and the inner one, which is preferably made of a non-woven fiber fabric. While such a product has proved to be completely satisfactory, there is the possibility that the product becomes saturated during use with urine, and it does not prevent the issuance of urine from the diaper. In addition, when the device is worn as a diaper engaged around the baby's legs, it is difficult to obtain a close adherence to the legs sufficient to block the passage of the urine. It is also difficult to obtain a diaper which will flex sufficiently during wearing so that it will become completely comfortable.

SUMMARY OF THE INVENTION

In accordance with the invention, a diaper is provided which includes an outer sheet of a waterproof plastic material which is deformed so as to form a cavity between the sides and ends of the sheet which extends inwardly a considerable distance, for example, about an inch from the surface of the sheet. An absorbent pad is placed in the cavity to absorb urine during wearing, and in addition, the inventive device includes moisture of liquid holding plastic strips which are welded along each side of the cavity to the marginal areas of a width such that they extend over the cavity and overlie the pad and prevent the outflowing of any urine which is contained in the cavity and held by the pad.

In accordance with a feature of the invention, the moisture holding strips are advantageously stretched during the time at which they are welded to the outer sheets, so that when the welding is completed they form a resilient holding strip which, when placed on each side of the cavity, provides leg engaging areas permitting resilience in wearing and tight holding to the baby's legs.

A further feature of the invention is the formation of the cavity with a bottom having corrugations or pleats so that the diaper may expand or contract or deform during use so that it may be worn without difficulty and discomfort.

The invention thus insures the obtaining of a better adherence of the diaper to the body of the baby and in particular better non-troublesome adherence of the side portions which embrace the baby's legs close to the groin. In addition, the mositure holding strips insure the obtaining of waterproof side barriers which prevent the outflow of the urine from the pocket. The undulations formed in the bottom of the cavity allow spreading out of the walls when the diaper is put on the baby's body, permitting flexing with the movement of the baby and easy retention of the pad.

Accordingly, it is an object of the invention to provide a diaper which comprises an outer sheet of waterproof plastic material having a deformed recess area between the sides and ends thereof forming a pad receiving cavity bordered by marginal areas on each side and on each end of the cavity, the cavity having a bottom spaced in an outward direction from said marginal area and containing an absorbent pad of substantially the same thickness, which is partly covered by a moisture holding strip of plastic which overlies at least a part of the marginal area on each side of the cavity and is welded to these marginal areas, and also overlies at least a portion of the absorbent pad.

A further object of the invention is to provide a diaper which is made of a waterproof plastic material and which has resilient leg engaging areas on each side, means for forming a pocket for containing liquids which contains an absorbent pad which is partly covered by a strip which extends over the top of the cavity and thus retains any liquid therein.

A further object of the invention is to provide a diaper which is simple in design, rugged in construction, and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the Drawings:

FIG. 1 is an exploded perspective view of a diaper constructed in accordance with the invention;

FIG. 2 is a front end interior perspective view of the diaper shown in FIG. 1;

FIG. 3 is a section taken along the lines III—III of FIG. 2; and

FIG. 4 is a section taken along the line IV—IV of FIG. 2.

GENERAL DESCRIPTION OF THE PREFERRED EMBODIMENTS

Referring to the drawings in particular, the invention embodied therein comprises a diaper generally designated 10 of a type which is sometimes referred to as a "diaper knicker" or a disposable diaper. The diaper 10 comprises an outer web or sheet 1 of a plastic waterproof material having a cavity 4 formed therein intermediate the sides and ends by a permanent deformation of the material. The cavity 3 leaves marginal areas 2 and 2' on respective long sides of the outer sheet 1 and 3 and 3' on respective shorter ends. In accordance with one feature of the invention, the bottom 4b of the cavity 4 is advantageously formed with either longitudinal corrugations or pleats 5 to facilitate the flexing and expansion and contraction of the cavity bottom as shown in FIG. 4, or the bottom 4b may be made substantially straight and flat as indicated in FIG. 3. The preferred construction is with corrugations arranged with a series of undulations extending transverse to the longitudinal direction. This permits an outward deflection of the outer wall 1 when the diaper is used. A resilient pad 6 is inserted into the cavity 4, and it is of a thickness comparable to the depth of the cavity which, for example, may be made from ½-2 inches thick, as desired. The pad 6 is advantageously made of a cellulose pulp fiber formed either by making successive windings of the pulp or by a superimposition and compression of one or more layers of fibers.

In accordance with a feature of the invention, a moisture holding strip 7 extends along the marginal side edges 2 and has a portion along its length which is welded to the side edges, leaving an unsecured or free portion 7a which extends over the pad on respective sides of the pad. The moisture holding strips function to insure that moisture or urine does not exit from the cavity 4 on each side and flow our through the diaper edges 12 and 12' which engage around the respective legs of the wearer.

In accordance with another feature of the invention, the motion holding strips 7 are advantageously pre-stretched before they are welded to the outer sheet 1 so that when the welding is completed they tend to compress the outer sheet in the area of the leg engaging portion so as to form resilient encompassing areas for engagement around the wearer's legs.

In the preferred method of the invention the strips are pre-stretched so as to cause a certain elongation thereof before they are superimposed over the marginal edges 2 and 2', and they are welded together with an inner layer of non-woven fabric 8 so as to close the cavity completely and to cover the two strips 7 in their pre-stretched condition. The welding is advantageously made so as to weld the inner layer 8, the strips 7, and the outer 1 to one another in the welded area designated a in FIG. 3.

The outer sheet or web 1 can be made of any waterproof plastic material of sufficient resistance. The moisture holding strips 7 are preferably formed from a polyethylene material, and the inner layer 8 is advantageously a non-woven fabric. The strips 7 of polyethylene can be made 15μ thick, and in such instances they would be stretched to an additional 10% in length for welding. Polyethylene is used for this type of product and is of low cost, but a material such as polyvinyl chloride, polyester, or polyprophylene may be used as desired.

It should also be appreciated that the welding between the strips 7 and the web 1 may be made along the whole overlying surface of the strip along the side edges 2 and 2'. Preferably it is made at certain selected areas along its length, and ends as indicated in the enlarged area shown at 9 in FIG. 2. Such welding is carried out on the square area shown in dark lines, and the white areas indicate the non-welded portions. The elongation of the strips at the area a can be changed in dependence upon the welded portion areas in relationship to the non-welded areas.

A fourth consideration of the invention is the length of the strip 7 which is employed to form the moisture holding strips in the amount of elongation it will be given before it is secured to the outer web 1 so as to vary the resilience of the areas in which it is welded to the outer strip.

Another important consideration is the width of the strip 7, and the amount of the strip which extends over the pad 6 and remains unsecured to the outer web 1. By making the strips of a waterproof plastic material, they are very effective to prevent the passage of the urine from the pad outwardly. This width is determined by the optimum exposure of the pad to the body of the user, counterbalanced by the necessity of retaining the moisture in the pocket during movement of the user.

With the inventive method, pre-stretching of the tape 7 before welding may be carried out in a continuous process because the strips can simply be unrolled from a reel by means of a simple device such as rollers, for instance, which will impart to the strip the necessary pre-stretching before welding. The welding can be carried out in the areas a simultaneously and at separate times with respect to the welding at the head edges 3 and 3'. After welding, the recovery of the strips 7 to its unstressed condition causes a slight crumpling of the length of the diaper knickers, and this makes the knicker adhere perfectly to the baby's body when the product is worn. Especially in the area a where the welding is carried out, the diaper will resiliently engage around the baby's legs without any constraint, and will aid in preventing any escape of liquid along with the waterproof edges 7a which overlie the pad 6.

While specific embodiments of the invention have been shown and described in detail to illustrate the application of the principles of the invention, it will be understood that the invention may be embodied otherwise without departing from such principles.

What is claimed is:

1. A diaper comprising an outer sheet of waterproof plastic material having a recessed area between the sides and ends thereof forming a pad receiving cavity bordered by marginal areas on each side and end, said cavity having a bottom spaced outwardly from said marginal areas, an absorbent pad disposed in said cavity, and a moisture holding strip of plastic overlying at least a part of a marginal area on each side of said cavity and at least a portion of each side of said pad and having at least a portion secured to the outer sheet along the length of said moisture holding strip.

2. A diaper according to claim 1 wherein said moisture holding strip is stretched before it is secured by being welded to said outer sheet so that it causes a slight crumpling of the outer sheet to provide leg-engaging resilient areas along the area of said moisture holding strips which is welded to said outer sheet.

3. A diaper according to claim 2 wherein said moisture holding strips are stretched to from 5 to 20% of their length prior to being welded to said outer sheet.

4. A diaper according to claim 1 wherein said moisture holding strips are made of a plastic material of one of the following: polyethylene, polyvinyl chloride, polyester, polypropylene, polyammides and other derivatives of polyolephines.

5. A diaper according to claim 1 wherein said moisture holding strip is of 10 to 30μ thick.

6. A diaper according to claim 1, including an inner sheet of non-woven fabric disposed over said cavity and said moisture holding strips and being welded to said outer sheet.

7. A diaper according to claim 1 wherein said moisture holding strips are welded only at spaced locations along the length of said strips to said outer sheet.

8. A diaper according to claim 7 wherein said welding comprises a grid pattern of welded and unwelded areas.

9. A diaper according to claim 1 wherein said other sheet has a pleat formation at the location of said cavity.

10. A diaper according to claim 9 wherein said pleat formation comprises a corrugation which is curved transversely to the length of said cavity.

11. A diaper according to claim 1 including a nonwoven fabric sheet overlying said outer sheet covering said cavity and said moisture holding strips, and a portion of said marginal areas on the sides and ends of said outer sheet and being welded to said outer sheet.

12. A process for making a diaper or similar sanitary product comprising forming an outer sheet with a cavity therein with a bottom spaced outwardly from marginal areas surrounding said cavities, and covering portions of each side of said cavity by first stretching a respective plastic strip for covering each side, and welding this strip to a respective marginal area on each side of the respective cavity so as to cause the strip after welding in recovery in its unstressed condition to crumple the outer sheet and form leg engaging resilient areas.

13. A process according to claim 12 wherein said strips are welded so as to leave portions thereof free to extend over said cavity and including placing an absorbent pad in the cavity before the strips are welded over the cavity.

14. A method according to claim 12 including forming a cavity by deforming the outer sheet and also providing undulations in the wall of the cavity during the deformation.

15. A disposable diaper comprising:
(a) an elongated water-proof plastic outer web having opposite sides and ends with a cavity formed therein which is elongated in the direction of elongation of the outer web, the outer web having side and end margin areas bordering the cavity;
(b) a resilient absorbant pad disposed in the cavity of a thickness approximately equal to the depth of the cavity;
(c) a pair of plastic prestretched strips extending along elongated sides of the cavity and welded to the outer web along the side margin areas thereof, each strip having a portion overlaying side portions of said pads for preventing liquid from leaving the cavity near the side portion of the pad; and
(d) a non-woven water-permeable inner layer disposed over the pad and welded to the strips and at least portions of the outer web margin areas.

16. A disposable diaper according to claim 15, further including pleats in the outer web cavity extending transversely to the longitudinal extent thereof.

* * * * *